US005328846A

United States Patent [19]

Wedler

[11] Patent Number: 5,328,846

[45] Date of Patent: Jul. 12, 1994

[54] METHOD FOR REMOVING EXOGENOUS DEPOSITS FROM HYDROPHILIC CONTACT LENSES

[75] Inventor: Frederick C. Wedler, State College, Pa.

[73] Assignee: The Penn State Research Foundation, University Park, Pa.

[21] Appl. No.: 138,884

[22] Filed: Oct. 18, 1993

Related U.S. Application Data

[63] Continuation of Ser. No. 821,726, Jan. 15, 1992, abandoned, which is a continuation-in-part of Ser. No. 721,057, Jun. 6, 1991, abandoned, which is a continuation-in-part of Ser. No. 389,037, Aug. 3, 1989, abandoned.

[51] Int. Cl.[5] ........................ C12S 1/00; D06M 16/00; C12N 9/28; C11D 1/00

[52] U.S. Cl. .................................... 435/264; 435/262; 435/202; 514/839; 252/174.12; 134/901

[58] Field of Search ........................ 435/262, 264, 202; 514/839; 252/174.12, 80, 82; 134/901

[56] References Cited

U.S. PATENT DOCUMENTS 4,614,549 9/1986 Ogunbiyi et al. ..................... 134/19
4,710,313 12/1987 Miyajima et al. ................... 514/839

FOREIGN PATENT DOCUMENTS 0093784 11/1983 European Pat. Off. .
0140669A1 6/1986 European Pat. Off. .

OTHER PUBLICATIONS

Chemical Abstracts, vol. 102:47688v (1985).
Chemical Abstracts, vol. 100:39653y (1984).
Chemical Abstracts, vol. 103:109984v (1985).
Wedler, et al., (1987) Clinical & Experimental Optometry, 70.2:59–68.
Violet, et al., (1989) Biochem. J. 263:665–670.
Konstantinov, et al., (1984) Comptes rendus de l'Academe burgare des Sciences, Tome 37, No. 9.
Nakayama et al "Cleaner for Contact Lenses" Patent Abstract of 59-52781 Oct. 1985.
Tschoepe, M. "Disinfecting and Cleaning Product . . . for the Care of Contact Lenses", CA110(14): 121492k Aug. 1988.
Tschöpe, M. EP 279401A2, English Translation, Aug. 1988.

*Primary Examiner*—Michael G. Wityshyn
*Assistant Examiner*—Timothy J. Reardon
*Attorney, Agent, or Firm*—Thomas J. Monahan

[57] ABSTRACT

The present invention describes a method and composition for removing exogenous mucin and protein-mucin deposits from hydrophilic contact lenses.

6 Claims, 8 Drawing Sheets

METHOD FOR REMOVING EXOGENOUS DEPOSITS FROM HYDROPHILIC CONTACT LENSES

This is a continuation of copending application(s) Ser. No. 07/821,729 filed on Jan. 15, 1992, now abandoned, which was a continuation-in-part of U.S. patent application Ser. No. 07/721,057 filed Jun. 26, 1991, now abandoned, which was a continuation of U.S. patent application Ser. No. 07/389,037, filed Aug. 3, 1989, now abandoned.

FIELD OF THE INVENTION

This invention relates to contact lens cleaning solutions and, in particular, to a method and composition for removing mucin and protein-mucin deposits from hydrophilic contact lenses.

BACKGROUND OF THE INVENTION

With the advent of hydrophilic or soft contact lenses, following the successful experiments of Wichterle and Seiderman reported in U.S. Pat. Nos. 2,979,576 and 3,721,657, respectively, the practitioner was given another means to correct visual impairments in his patient population. The main virtues of these lenses were their ease of manufacture, their complete transparency and their increased comfort to the user when compared with hard plastic lenses developed much earlier.

The earliest soft lenses offered commercially in the 1970's were made from polar monomers, e.g., hydroxyethylmethacrylate (HEMA), polymethylmethacrylate (PMMA), or polyvinylpyrrolidone (PVP) polymeric materials having the appearance of soft, transparent hydrogels. Within the past several years, however, other materials such as various silicone based polymers have become available and used for the manufacture of soft lenses.

The increased comfort experienced by the user which has resulted in near universal acceptance of soft contact lenses is brought about by the ability of the lens to absorb water. These lenses, when viewed under high power microscopy, appear as a highly porous matrix. When the lens is swelled in aqueous solutions prior to its initial use by the patient, this polar matrix allows the lens to absorb large quantities of water, in excess of 100 per cent of the weight of the dry lens. Consequently when placed on the eye, the user does not experience the discomfort of the foreign object in the eye but rather experiences the somewhat cooling sensation of the additional fluid being added to the eye.

The water-compatible properties which provide user comfort also are the basis for binding of exogenous materials, leading to formation of deposits on the anterior (air-exposed) surface of the lens. Deposit buildup may be exacerbated by conventional aseptization methods, with hazing of vision, loss of optical acuity, and moderate to severe eye irritation. Deposit formation is a primary cause of dissatisfaction by roughly ⅓ of the lens wearing population to adapt successfully to soft contact lenses. These statistics also make it clear that currently available cleaning methods are inadequate for dealing with problems experienced by patients classified as "heavy" depositors.

In the early 1970's it was first demonstrated that deposits on hydrophilic lenses contained proteins found in the normal human tear fluid. These data were summarized in a 1982 review article by F. C. Wedler & T. Riedhammer, "Soft Contact Lenses: Formation of Deposits," [in CRC Critical Reviews on Biocompatibility, Vol. II, chapter 3, pp. 31–46, CRC Press, Boca Raton, Fla. ] the disclosure of which is hereby incorporated by reference. These findings also refuted the belief that these deposits were bacterial plaques which would, if the "contaminated" lens were not replaced, cause infection and damage to the eye.

Until fairly recently, methods for separation, purification, detection, and quantification of sub-microgram levels of bio-materials obtained from soft contact lenses did not exist. In 1987, biochemical techniques were developed for quantitative analysis of biomaterials deposited on single patients lenses [F. C. Wedler, D. Horensky, B. L. Illman & M. Mowrey-Mckee, "Analysis of protein and mucin components deposited on a hydrophilic contact lenses", Clin. Exptl. Optom., 70: 59–68]. Substantial amounts of tear fluid proteins were detected on "normal" patient lenses with which hazing and eye irritation were not observed. The four major tear fluid proteins detected in these studies were albumin, lysozyme, lactoferrin, and pre-albumin. The most important discovery arising from this works was that "heavy lens deposits did not correlate with deposition of tear fluid proteins, but did coordinate strongly with mucin, a heterogeneous mixture of derivatized polysaccharides.

Prior to this finding, it was believed that proteinaceous materials were the main cause of irritating lens deposits, and based on this, protein-degrading enzymes (proteases) were used in cleaning solutions to remove these irritating deposits. Indeed, U.S. Pat. No. 3,910,296 discloses and claims the use of protease-containing solutions for soft contact lens cleaning. Included in this formulation were sulfhydryl-group containing compounds, needed to activate the protease (papain) and which could also reduce disulfide bonds in the protein substrate, but which have an offensive "rotten egg" odor.

A number of subsequent disclosures have sought to improve on the basic concept of protease-based cleaners. These additional disclosures suggest that other substituents be added to the cleaning solution, that the condition under which cleaning occurs be adjusted, or both. For example, U.S. Pat. No. 4,096,870 suggests the use of the digestive aid pancreatin, a crude mixture of hydrolytic enzymes extracted from hog pancreas, formulated in combination with boric acid and sodium chloride as a cleaning mixture. U.S. Pat. No. 4,285,738 suggest the use of a hypertonic solution of urea and/or a guanidine salt added to the protease formulation along with a sulfhydryl compound or other suitable reducing reagent capable of cleaning disulfide bonds.

Commercially available products for enzymatic cleaning of soft(hydrophilic) contact lenses include, for example, OPTI-ZYME TM (Alcon Laboratories) based on porcine pancreatin as the active ingredient, and ALLERGAN ENZYMATIC TM, EXTENZYME TM, and PROFREE/GP TM (Allergan Pharmaceuticals) based on papain.

Now that the major cause of extraneous heavy lens deposits is known to be mucin, not proteins, it becomes clear why the majority of currently available commercial enzyme-based cleaners fail to remove heavy deposits. Although the enzymes contained in these cleaners will specifically attack and degrade proteinaceous materials, they are ineffective against mucin, which is a heterogeneous mixture of complex carbohydrates (mucopolysaccharides) and carbohydrate surrounding a protein core (glycoproteins).

Since presently available enzyme-based cleaning solutions fail to degrade or remove mucin deposits from soft contact lenses, there is obviously a need to develop a new, second-generation cleaner, based on mucin-degrading enzymes. These mucin degrading enzymes could be used either alone or in combination with proteases to enhance the cleaning of heavily deposited hydrophilic lenses.

SUMMARY OF THE INVENTION

A composition is described for removing heavy deposits from a contact lens, the deposits being mucin or mucin-containing. The composition includes a mucin degrading enzyme consisting of alpha-amylase as derived from *Bacillus licheniformis*. The composition is used in a contact lens cleaning solution at room temperature to remove the deposits.

DETAILED DESCRIPTION OF THE INVENTION

Figure 1:
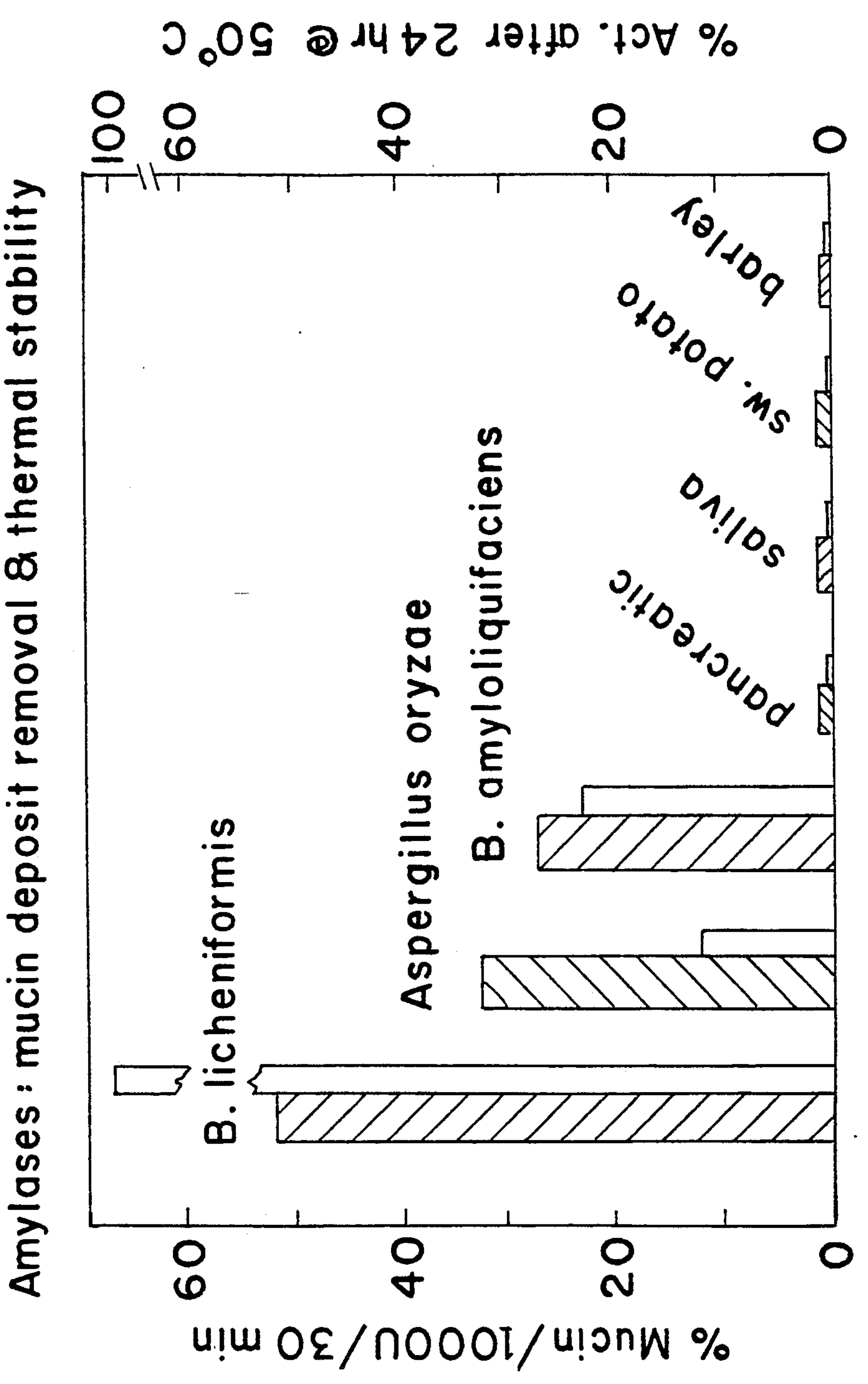
FIG. 1 is a chart that plots both percent of mucin removal per 1000 U per 30 minutes (filled bars correspond to left axis) and the percent activity after 24 hours (open bars correspond to right axis) at 50° C. for various alpha-amylases.

Essential for proving the efficacy of any composition or method for degrading and removing mucin from hydrophilic lenses are sensitive, accurate assay methods. Two such methods were developed in the present work, both based on use of radioactively labeled mucin or mucin/protein. The first involves deposition onto new hydrophilic lenses of a synthetic mixture of components designed to model human tear fluid, including radiolabeled mucin. The second is based on direct radiolabeling of mucin and other components deposited on patient worn lenses.

Based on the known composition of human tear fluid, a synthetic solution to mimic human tear fluid was formulated with the following pure constituents—obtained commercially (Sigma Chemical Co.) or purified according to published procedures—in PBS (phosphate-buffered saline: 10 mM phosphate, pH 7.4, 3 mM KCl, 120 mM NaCl):

| | | |
|---|---|---|
| 0.225 mg/ml | albumin(Bovine serum) | 20 mM KCl |
| 0.075 mg/ml | lysozyme (hen egg white) | 1.0 mM $CaCl_2$ |
| 0.075 mg/ml | lactoferrin (bovine colostrum) | 0.5 mM $MgCl_2$ |
| 0.010 mg/ml | pre-albumin (human serum) | 0.1 mM $MnCl_2$ |
| 40 mg/ml | [$^{14}$C]- labeled mucin | 0.1 mM $ZnCl_2$ |

The radiolabeled mucin was produced by succinylation of bovine submaxillary mucin (75 mg/ml) in pH 8.0 carbonate buffer with 0.25M [$^{14}$C]-succinic anhydride (250 uCi).

Protein-mucin model deposits were produced by applying this synthetic tear fluid mixture to new (unworn) hydrophilic contact lenses according to the following example:

EXAMPLE I

Preparation of Model Mucin/Protein-deposits on Hydrophilic Lenses

Typically, a group of 12 lenses were presoaked for 1 hr in PBS. Lenses were then blotted dry and placed individually in wells of a porcelain spot-test plate. Over the exposed concave surface of each lens, a total of 0.1 ml of the above synthetic tear fluid/mucin mixture was then applied in 5×0.02 ml aliquots, distributed evenly with the end of a fire polished glass rod and evaporated to dryness in a stream of warm air, without drying the interior portions of the lenses. Deposited lenses were soaked and stored individually in 2 ml of PBS solution.

Patient worn hydrophlic lenses, classified as being "heavily" deposited, were subjected to direct in vitro labeling with [$^{14}$C]-succinic anhydride. This approach, which [$^{14}$C]-labels both protein and mucin components, was carried out according to the following example:

EXAMPLE II

Radioactive Succinylation of Mucin/Protein on Patient-worn Lenses

Typically, 12 patient-worn, heavily deposited lenses were presoaked in pH 8.0 carbonate buffer for 1 hr, blotted dry, and placed individually, with the anterior (deposited) side down, in the wells of a porcelain spot-test plate, each of which contained 25 1 of 0.25M [$^{14}$C]-succinic anhydride (250 Ci/ml) dissolved in anhydrous dioxane, and were allowed to react for 30 min at room temperature. The lenses were then each soaked individually in 3×100 ml of PBS to dissolve and dialyze away any unreacted labeled small molecules, after which each was stored in a vial with 1.0 ml PBS.

Studies were undertaken to determine the efficiency with which certain enzymatic agents can remove mucin and other components from hydrophilic contact lenses, using radiolabled deposits produced according to the methods described in either Example I or Example II above. A number of the candidates tested for ability to remove mucin were enzymes, commercially available in quantity, that were specific for a variety of carbohydrate polymers. The most likely ones included two enzymes known to degrade the constituents of mucin (glycoproteins and mucopolysaccharides), neuraminidase and hyaluronidase, both isolated from pathogenic micro-organisms. In addition, a number of other hydrolytic enzymes known to degrade carbohydrate polymers were tested, including pectinase and two amylases. The general assay procedure for these studies is outlined in the following example:

EXAMPLE III

Assay for Removal of Mucin from Hydrophilic Lenses

In a typical test for mucin removal, model deposited lenses (5 per group) prepared as described in Example I, were presoaked in PBS for 1 hr, then cut into two equal pieces. As a control, the first ("before") half lens was soaked in PBS lacking enzyme for 1 hr at 30° C. The second ("after") half was placed in 1.0 ml of PBS containing the desired mixture of enzymes (see below) and was then incubated for 1 hr. at room temperature. The amount of [$^{14}$C]-mucin remaining on a half lens was determined by heating it at 95° C. for 30 min in 2.0 ml PBS containing 1% sodium dodecyl sulfate and 2 mM dithiothreitol, then counting this solution in a water-compatible liquid scintillation cocktail. The amount of [$^{14}$C]-mucin remaining on the "before" portion of the lens was taken as 100% and was compared to that on the "after" sample.

A number of different hydrolytic enzymes were tested as possible candidates for mucin removal. Surprisingly, the two enzymes reported to be specific for mucin components, neuraminidase (Sigma, type V) and hyaluronidase (Sigma, type II,) used individually or in combination, removed less than 5% of the mucin in model deposits or on patient-worn lenses. These negative results, plus the difficulties involved in providing these enzymes as a safe commercial product, economically priced for the consumer, indicated the need to identify an alternative enzyme system, commercially available in quantity, that can effectively remove mucin deposits from hydrophilic contact lenses.

The data in Table I also indicate that protease alone was relatively ineffective in removal of these biomaterials, especially with patient-worn lenses. Of the commercially available hydrolytic enzymes tested for ability to remove mucin or protein/mucin deposits, the most dramatic (but unexpected) positive results were produced by alpha-amylase (Sigma, type XII-A; *Bacillus licheniformis*) . In addition, alpha-amylase combined with subtilisin (used in currently available enzyme-based lens cleaners) exhibits enhanced or synergistic removal of mucin/protein deposits.

TABLE 1

Tests of Enzymic Removal of Mucin/Protein from Hydrophilic Lenses

| Abbrev. | Enzyme(s) | % Removed/hr Model deposit | % Removed/hr Patient Lenses |
|---|---|---|---|
| (aA) | alpha-Amylase (Sigma, type XII-A, 880 U) | 13 | 7 |
| (bB) | beta-Amylase (Sigma, type I-B, 1000 U) | 0 | 0 |
| (Pa) | Papain (Allergan tablet) | 42 | 10 |
| (Pc) | Pectinase (Sigma, Asp. niger, 110 U) | 0 | 0 |
| (Se) | Subtilisin (B & L Renu effervescent tablet) | 32 | 0 |
| aA + Se | alpha-Amylase + subtilisin | 55 | 14 |
| aA + Pa | alpha-Amylase + papain | 45 | 5 |

Separate tests were performed with model deposited lenses (Example I) to determine the effect of time and increased units of enzyme on the extent of deposit removal for the enzymes alpha-amylase and subtilisin, as shown in Table II:

TABLE II

Time Dependence of Enzymic Mucin Removal from Hydrophilic Lenses

| | Soak time (min) | % Removed |
|---|---|---|
| a) Subtilisin (B & L Renu tablet) | 30 | 30 |
| | 60 | 42 |
| | 120 | 70 |
| b) Alpha-Amylase (Sigma, 10,000 U) | 30 | 47 |
| | 60 | 57 |
| | 120 | 65 |
| | 240 | 78 |
| | 300 | 92 |

The data reported in Tables I & II indicate that the commercial protease-based cleaner removed less than 50% of the deposit in 1 hr, but that 10 mg of alpha-amylase (specific activity 1000 U/mg) alone was capable of removing 65% of the deposited mucin in 2 hr and more than 90% in 5 hr. The time required for complete (100%) removal could, of course, be shortened by using an increased amount of alpha-amylase. Table 1 further indicates that mucin on patient-worn lenses is more tenaciously bound than with model deposits.

Alpha-amylase has been demonstrated to be specific for internal alpha-1,4 glucan bonds of linear homologous polymers of underivatized D-glucose [T. Tagaki, T. Hiro, & T. Isemura (1971) in "The Enyzmes" 3rd edn (P. D. Boyer, ed), vol V, pp. 235–271, Academic Press, New York]. Mucin however, is a highly heterogeneous, branched mixture of mucopolysaccharides and glycoproteins, composed of highly derivatized saccharides linked with alpha- and beta-1,3- and 1,4- type glucan bonds. Based on this, the finding that alpha-amylase is efficacious for removal of mucin and mucin/protein deposits from hydrophilic contact lenses is clearly not one that would be obvious to a worker of ordinary skill in the art.

The properties of alpha-amylases from different sources were tested to determine their stability and comparative mucin-removing capabilities. Alpha-amylases from the following sources were obtained from Sigma Chemical Co.: *Bacillus licheniformis* (also obtained as "Takatherm" from Solvay-Miles Co.)., Bacillus amyloliquifaciens, Aspergillus oryzae, porcine pancreas, human saliva, sweet potato, and barley malt.

The ability of these alpha-amylases to degrade model mucin deposits on generic (tetrafilcon A) soft contact lenses was assayed by dissolving 1000–1500 U of each enzyme in 2.0 mL of a pH 7.4 buffer solution, separately incubating at least 3 lenses, each deposited with labeled mucin, in each of these enzyme solutions for 30 and 90 min. at room temperature, then determining the % mucin removed, based on a known amount of labeled material deposited on each lens. Controls included soaking in a pH 7.4 buffer solution alone for 30 and 90 min.

The thermal stability of various amylases from different sources was determined by assaying solutions of these enzymes with identical amounts of protein present (in pH 7.4 buffer solution), incubating for 24 hrs. at 50° C., then reassaying for amylase activity.

In FIG. 1, both the percent of mucin removal per 1000 U, per 30 minutes and the percent activity after 24 hours at 50° C. are plotted for the amylases tested. The left hand bar for each amylase corresponds to the left vertical axis of the chart and the right hand bar corresponds the right vertical axis. Clearly alpha-amylase (*B. licheniformis*) is the only alpha-amylase that is both highly active and stable at moderately elevated temperatures (i.e., would be expected to have a reasonable shelf-life at room temperature in a liquid formulation).

As a preparation for the removal of mucin or mucin/-protein deposits from hydrophilic contact lenses, the hydrolytic enzymes may be compounded alone or in combination with other existing cleaning systems for hydrophilic contact lenses. For example, the data in Table II, taken with those in Table I, indicate the enhanced effect of using alpha-amylase plus subtilisin for removal of heavy mucin/protein deposits. By "compounded" is meant that the mucin degrading enzymes may have additional materials such as conventional excipients, antimicrobial agents, buffers stabilizers, or other materials conventionally used with hydrophilic contact lens cleaners in order to increase the shelf life of a commercial product, prevent damage to the lens material, make the cleaning composition more acceptable to the user, or allow for the cleaning composition to be manufactured in a specific form such as tablets, liquids, or powders. Of course, since these lenses must be maintained in aqueous solution, the cleaning system according to the present invention will be used as a solution, so that should the enzyme be compounded and sold as a tablet or powder, it will be necessary for the tablet or powder to be dissolved into an aqueous solution prior to its use. The exact amount of mucin-degrading enzyme present in the cleaning system any vary over a wide range, the amount depending upon the speed of cleaning desired. Neither the additional materials (which are well known to persons aware of the contact lens cleaning art) nor the amounts of mucin-degrading enzymes (which are a matter of choice to suit the specific purposes of the manufacturer) used in a hydrophilic contact lens cleaning system according to the present invention are necessarily critical. The amount of mucin-degrading enzyme present in a given formulation will necessarily be determined by the amount needed to clean the lens within the period of time chosen, as preferred by the manufacturer to satisfy the customer's needs.

To determine the efficiency of mucin removal on the four major types of soft contact lenses (i.e. Group I-non-ionic, low water; Group II - non-ionic, high water; Group III- ionic, low water; and Group IV -ionic, high water), each type was subjected to immersion in an alpha-amylase solution. Progress curves of labeled mucin from model lenses (of the aforesaid types of lenses) indicate that 3500 Units of alpha-amylase enzyme *B. licheniformis* will remove greater then 50% of mucin in 90 minutes for Group I, III and IV lenses and approximately 70% for Group II lenses. The rate and extent of mucin removal from Group II lenses was consistently 1.5–2.0 x higher than for the other three types at all levels of alpha-amylase. After enyzmatic treatment, a mechanical finger rub increased the percentage of mucin removal to better than 95%.

Alpha-Amylase comparison against commercial lens cleaners

A group of commercially-available soft contact lens cleaners were prepared according to the instructions provided, then assayed for total units (U) of amylase activity (cf. "Methods in Enzymology, " Vol. 1 (Colowick & Kaplan, eds.), p. 149ff, Academic Press, New York, 1955). Alcon Optizyme (pancreatin, an extract of porcine pancreas containing amylase, protease, and lipase) showed 108 U amylase activity, whereas Bausch and Lomb Renu (subtilisin, known to contain some amylase as contaminant) showed slight activity, and Allergan Enzymatic (papain, a Cys protease) and Barnes-Hind Softmate (subtilisin) showed negligible amylase activity (<10 U/tablet). In addition to comparing the alpha-amylase and commercial lense cleaners on model-deposited lenses, comparisons were made with patient-worn lenses as follows.

Experimental Methods

Formation of layered model deposits

New contact lenses (Wesley-Jessen, type I) were soaked overnight in phosphate-buffered normal saline (PBS) containing the mixture of salts used to favor protein deposition (see above—artifical tear solution). Each lens was then flipped into a concave shape and the posterior side placed in the bottom of the depression of a porcelain spot test plate (12 place). Under a steam of warm air, 0.025 mL of the artificial tear fluid proteins mixture (25x-concentrated) was pipetted onto the concave, anterior surface of the lens, distributed with the smooth end of a glass rod and dried, without allowing the lens to curl. The 0.025 mL of 80x-concentrated mucin (bovine submaxillary, labeled with $^{14}C$-succinic anhydride, was pipetted onto the anterior lens surface, distributed, and dried. The lens was then heated to 80°–85° C. for 1 hr., then placed in 2.0 mL of phosphate-buffered saline for storage. This procedure resulted in 63% (±3%) of the ($^{14}C$)-mucin applied to the lens actually remaining attached firmly to it.

($^{14}C$)-Succinylation of patient-worn lenses

Patient-worn lenses, all classified as "heavily" deposited were obtained from a clinic. Each was removed from its storage solution and soaked in a buffer solution composed of equal volumes of 5 mM phosphate, pH 7.0, and 1.0M sodium carbonate, pH 8.0. Unlabeled succinic anhydride (300 uL of 1 mg/mL in dry dioxane) was then added to a vial of labeled material (50 uCi, Amersham, 1,4-$^{14}C$ succinic anhydride). Then 20 uL samples of this solution was pipetted into the depressions of a 12-place porcelain spot-test plate, immediately after which the anterior (deposited) surface of a lens (dried on the surface with a lint-free KimWipe) was placed in contact with the succinic anhydride/dioxane solution, and allowed to react at room temperature for 30 min. The lens was then transferred and soaked in three changes, of 5.0 mL each, of PBS for 1 hr each, then transferred to 2 mL PBS for storage at 4° C.

Enzymic treatment of patient lenses and model deposits

Lenses (either $^{14}C$-succinylated patient-worn or model $^{14}C$ mucin-deposited) were soaked for one hour in 5 mL of PBS, then transferred to a vial containing (a) 2 mL of PBS with 10,000 International Units (IU) of *Bacillus licheniformis* alpha-amylase (ca. 10 mg of Solvay Takatherm or Sigma Type XIIA, dialyzed vs. PBS) or (b) 2 mL of the Allergan Enzymatic TM commercial cleaner, prepared as described for patient use. At the end of each time interval, each lens was grasped with tweezers, briefly swirled in the solution, then transferred to an identical solution for the next incubation period. These solutions were then mixed with a scintillation cocktail and counted for $14_C$. Any labeled material remaining on the lenses was removed by brief exposure to 1N NaOH then heated in 1% SDS at 95° C. for 15 min. The total $^{14}C$ counts removed were then calculated and plotted as a function of time. Lenses similarly treated were also photographed before and after similar treatment with alpha-amylase.

Results

Figure 2:
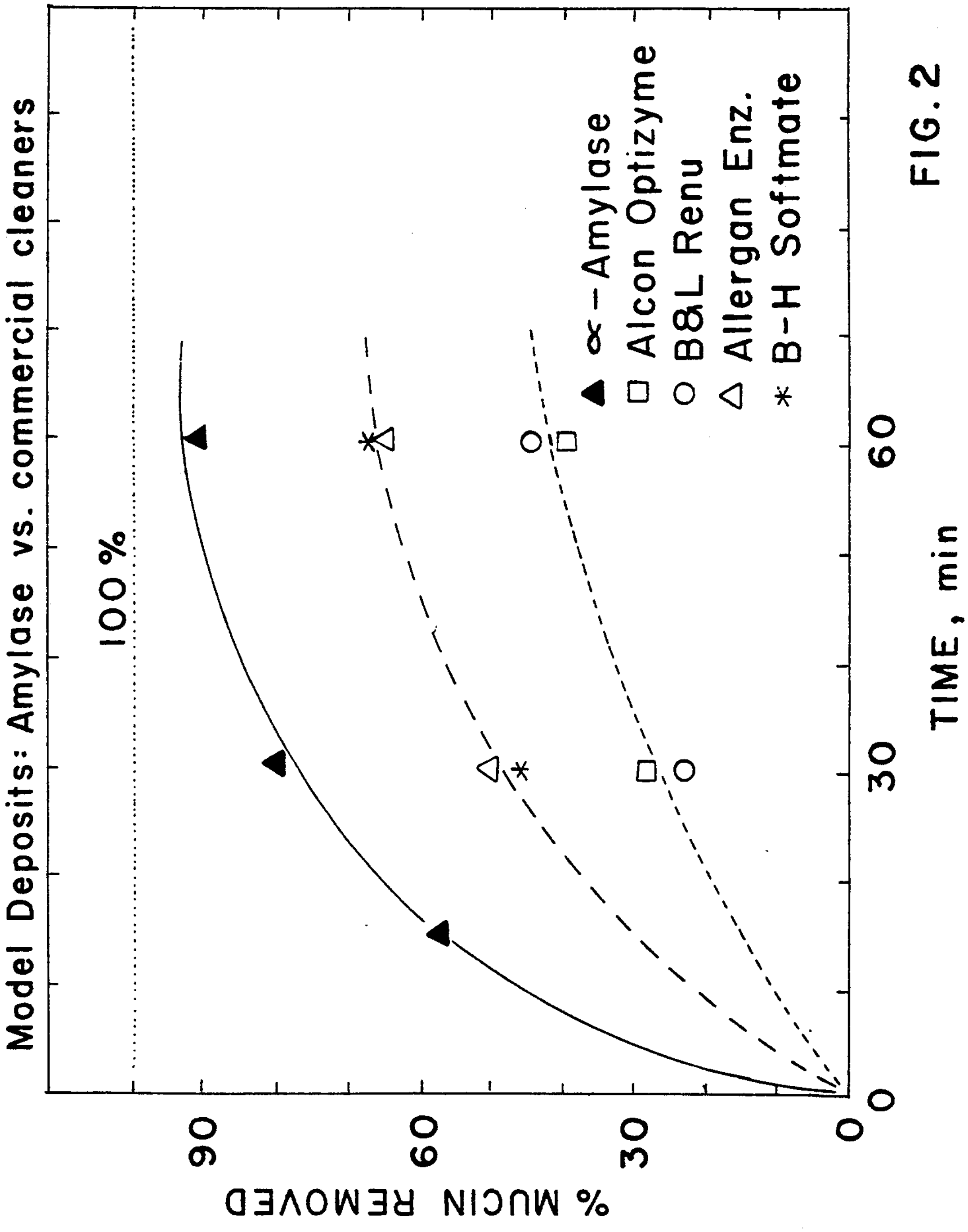
FIG. 2 is a chart that plots percent of mucin removed versus time (60 minutes) for various commercial lens cleaners and alpha-amylase.
Figure 3:
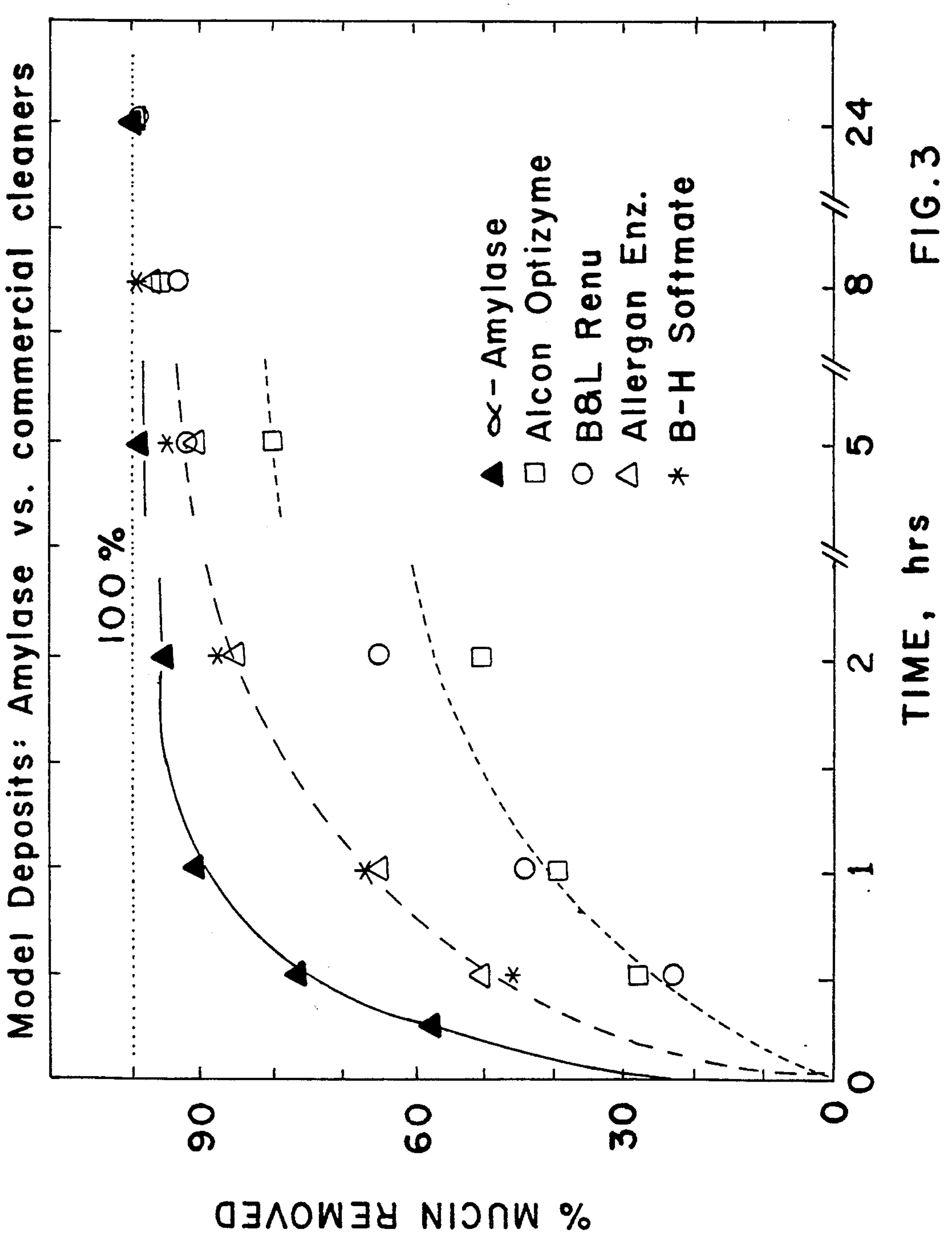
FIG. 3 is a chart similar to that of FIG. 2, but plotted over 24 hours.

FIG. 2 illustrates the % of mucin removal for all of the tested lens solutions (using model deposits) over 60 minutes. FIG. 3 is the same plot, but extended over 24 hours. As is clearly shown in FIGS. 2 and 3, over both a relatively short time, and longer times, 10,000 U (ca. 10 mg) of alpha-amylase (*B. licheniformis*) provided percentages of mucin removal superior to any of the tested commercial lens cleaners.

Figure 4:
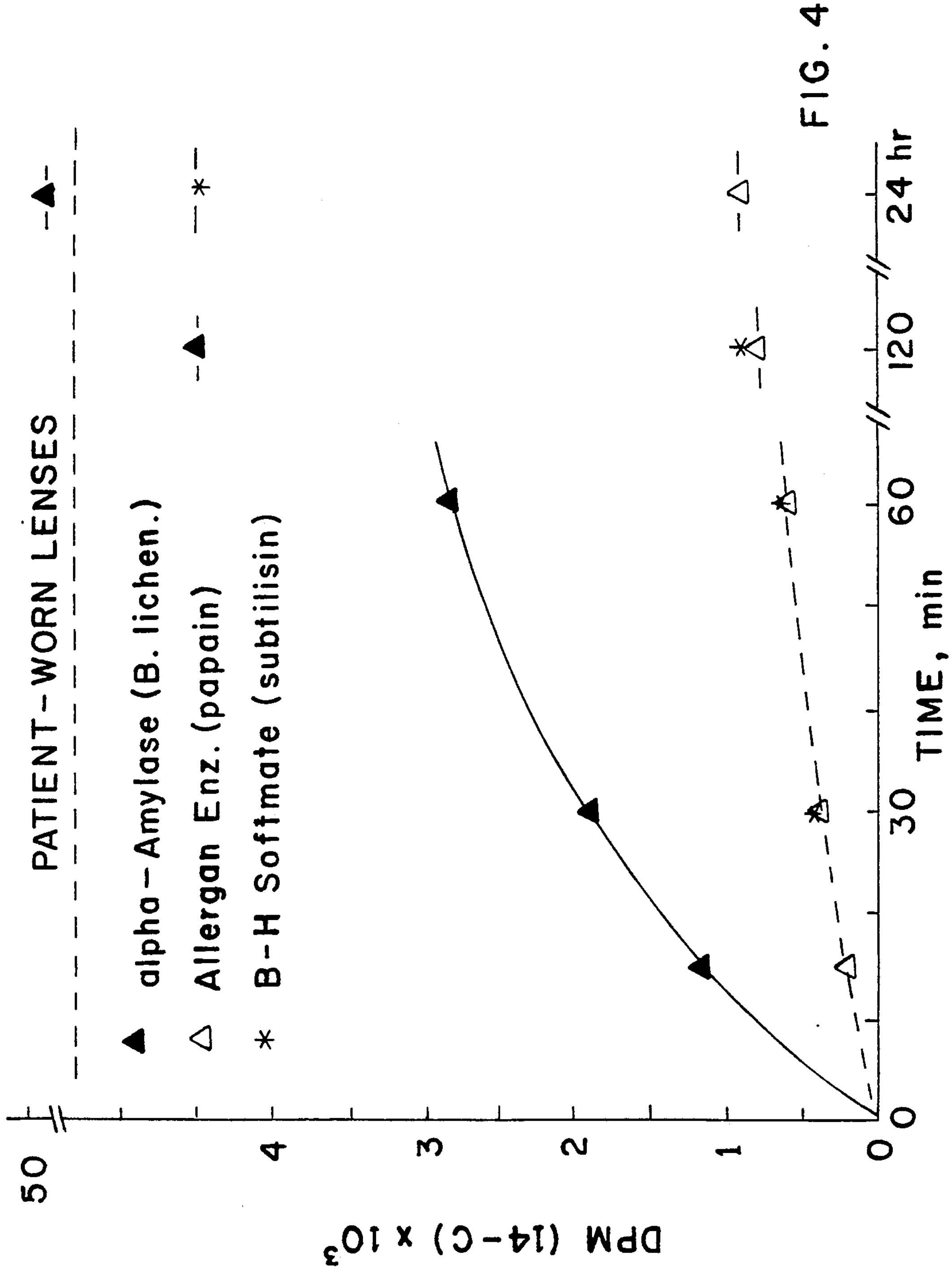
FIG. 4 is a chart that plots release of scintillation counts from radio-labelled mucin deposited on patient worn contact lenses, when treated with alpha-amylase and other commercial lense cleaners.
Figure 5A:
FIGS. 5A–5C, 6A–6C, 7A–7C and 8A–8C are photographs of patient-worn lenses with the lenses of FIGS. 5A, 6A, 7A and 8A being before treatment; the lenses of FIGS. 5B, 6B, 7B and 8B being after a 4 hour soak in a pH 7.4 buffer solution with 5000 U alpha-amylase at 25° C.; and the lenses of FIGS. 5C, 6C, 7C and 8C being lenses of FIGS. 5B, 6B, 7B and 8B after a 20 second finger rub.
Figure 5B:
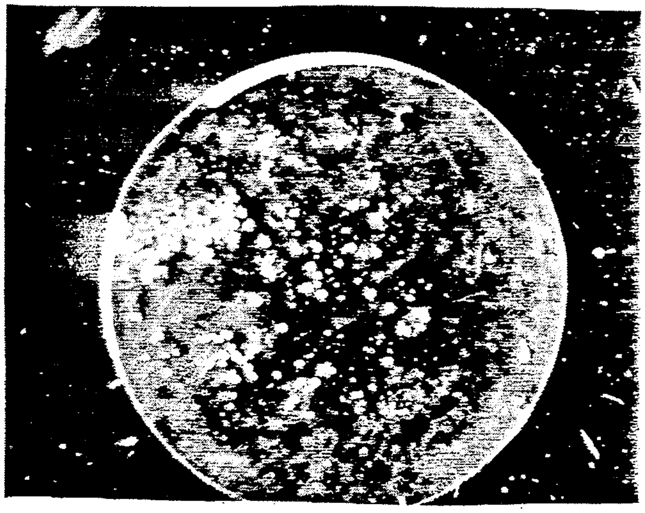
Figure 5C:
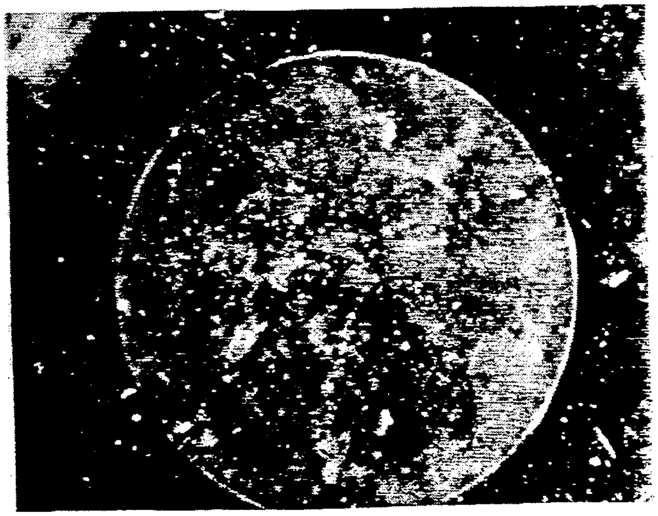
Figure 6A:
Figure 6B:
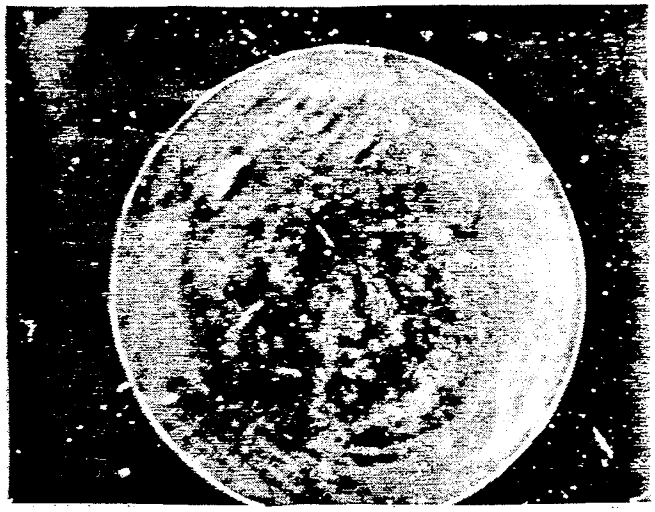
Figure 6C:
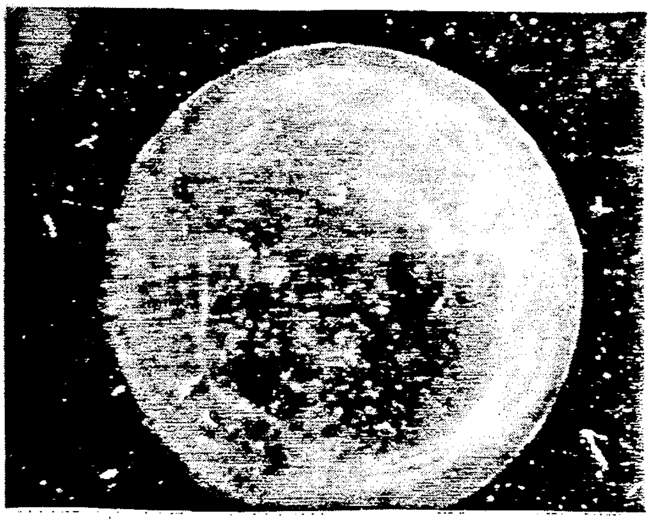
Figure 7A:
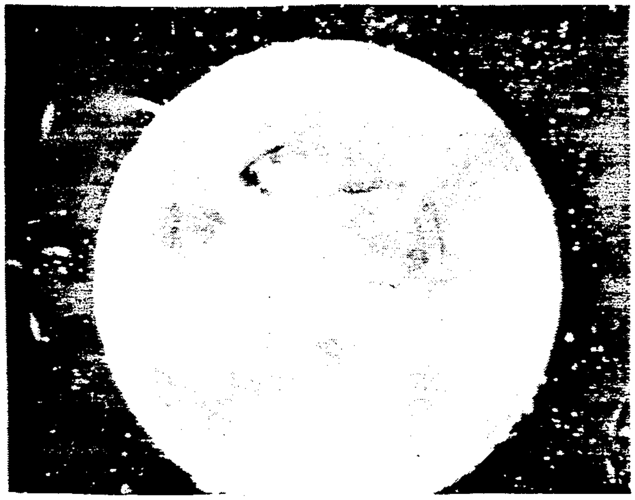
Figure 7B:
Figure 7C:
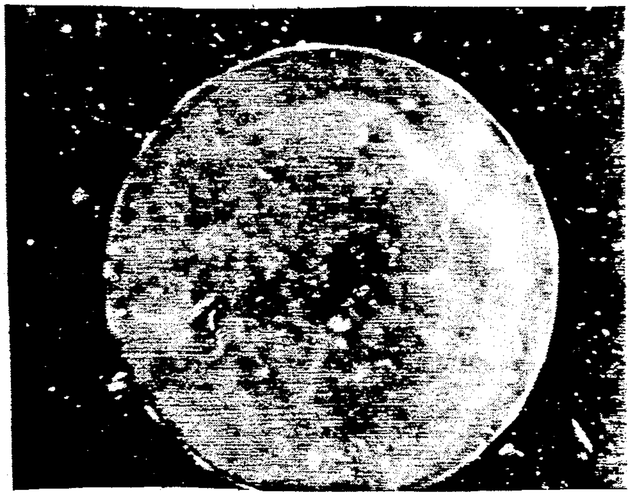
Figure 8A:
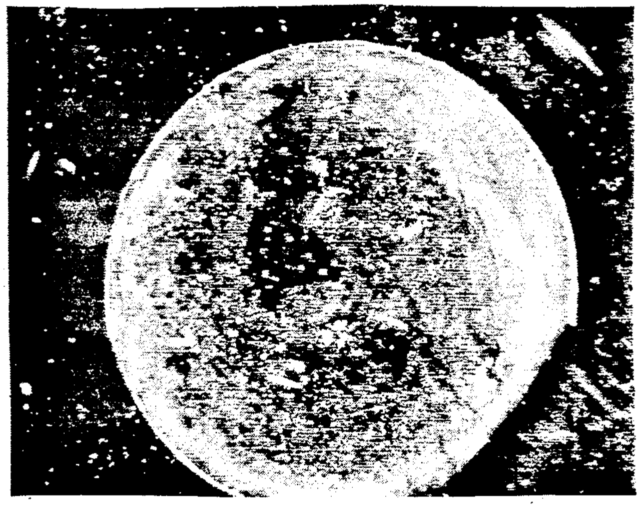
Figure 8B:
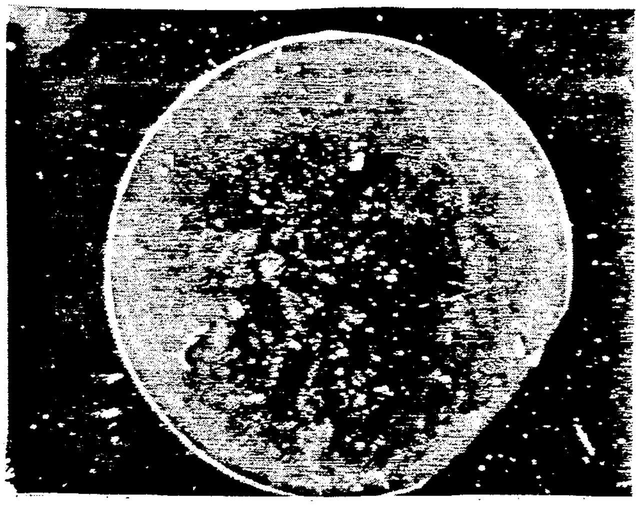
Figure 8C:

FIG. 4 illustrates relative levels of labeled mucin removed, over time, from patient-worn lenses when subjected to alpha-amylase (*B. licheniformis*) and several commercial lens cleaners (i.e. Allergan Enzymatic and Barnes-Hind Softmate). Here again, the alpha-amylase was clearly superior. In the chart of FIG. 4, disintegrations per minute of $14_C$ mucin removed from patient lenses was plotted against time.

FIGS. 5A–5C, 6A–6C, 7A–7C and 8A–8C are comparative photographs ( at 5× magnification) of four heavily deposited, patient-worn contact lenses. In the Figs., the lenses of FIGS. 5A, 6A, 7A and 8A are before treatment; the lenses of FIGS. 5B, 6B, 7B and 8B are after 4 hours of soak in a pH 7.4 buffer solution with 5000 U of alpha-amylase (*B. licheniformis*) at 25° C.; and the lenses of FIGS. 5C, 6C, 7C and 8C are the lenses of FIGS. 5B, 6B, 7B and 8B after a 20 second finger rub. Clearly in all instances, the alpha-amylase, at a minimum, sufficiently loosened the mucin deposit to a point where it could be removed with a finger rub. In most of the lenses, the soak alone was sufficient to remove substantially all of the deposit.

Thus, while I have illustrated and described the preferred embodiments of my invention, it is to be understood that this invention is capable of variation and modification, and I therefore do not wish to be limited to precise terms set forth, but desire to avail myself of such changes and alterations which may be made for adapting the invention to various usages and conditions. Accordingly, such changes and alterations are properly intended to be within the purview of the following claims.

Having thus described my invention and the manner and process of making and using it, in such full clear, concise and exact terms so as to enable any person skilled in the art to which it pertains, or with which it is most nearly connected, to make and use the same.

I claim:

1. A method for removing mucin and mucin-containing deposits from a contact lens, which method comprises:

providing a contact lens cleaning solution comprising a buffering agent, a mucin degrading enzyme and calcium ions in an amount sufficient to maintain said enzyme's stability, said mucin-degrading enzyme consisting of alpha-amylase from *Bacillus licheniformis,* in an effective amount sufficient to remove a mucin or mucin-containing deposit from a contact lens;

placing a contact lens having a mucin or mucin-containing deposit in contact with said cleaning solution at or near room temperature; and allowing a sufficient period of time to elapse to allow for said removal.

2. The method of claim 1 wherein the solution contains a protease suitable for removing a proteinaceous deposit from a contact lens.

3. The method of claim 1 with the added step of:

finger rubbing said contact lens to remove mucin and mucin containing deposits, said finger rubbing occurring when said contact lens is in contact with said cleaning solution.

4. A method for removing mucin and mucin-containing deposits from a contact lens, which method comprises:

providing a contact lens cleaning solution comprising a mucin-degrading enzyme composition consisting essentially of alpha-amylase from, *Bacillus licheniformis,* said alpha-amylase from *Bacillus licheniformis* present in an effective amount sufficient to remove a mucin or mucin-containing deposit from a contact lens, said contact lens cleaning solution further including a buffering agent and calcium ions in an amount sufficient to maintain enzyme stability;

placing a contact lens having a mucin or mucin-containing deposit in contact with said cleaning solution at or near room temperature; and allowing a sufficient period of time to elapse to allow for said removal.

5. The method of claim 4 wherein the solution contains a protease suitable for removing a proteinaceous deposit from a contact lens.

6. The method of claim 4 with the added step of:

finger rubbing said contact lens to remove mucin and mucin containing deposits, said finger rubbing occurring when said contact lens is in contact with said cleaning solution.

* * * * *